US006677431B2

(12) United States Patent  
DeGrado et al.

(10) Patent No.: US 6,677,431 B2
(45) Date of Patent: Jan. 13, 2004

(54) DESIGN, PREPARATION, AND PROPERTIES OF ANTIBACTERIAL β-PEPTIDES

(75) Inventors: William F. DeGrado, Media, PA (US); Yoshimoto Hamuro, San Diego, CA (US); Dahui Liu, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 09/732,911

(22) Filed: Dec. 11, 2000

(65) Prior Publication Data

US 2002/0132766 A1 Sep. 19, 2002

Related U.S. Application Data

(60) Provisional application No. 60/170,110, filed on Dec. 10, 1999.

(51) Int. Cl.[7] .................. A61K 38/04; A61K 38/16; C07K 7/02; C07K 14/00; C08H 1/00

(52) U.S. Cl. ................ 530/326; 514/13; 514/14; 514/15; 514/16; 514/17; 530/327; 530/328; 530/329; 530/332; 530/345; 525/54.1

(58) Field of Search .............. 422/28, 382, 383, 422/475, 501, 502; 514/2, 13, 14, 15, 16, 17; 530/326, 327, 328, 329, 332, 345; 525/54.1, 54.11

(56) References Cited

U.S. PATENT DOCUMENTS

| 5,683,868 A | 11/1997 | LaRossa et al. ............ 435/6 |
| 5,847,047 A | 12/1998 | Haynie ................ 525/54.1 |
| 6,060,585 A | 5/2000 | Gellman et al. .......... 530/323 |

FOREIGN PATENT DOCUMENTS

WO  WO 97/47593  12/1997

OTHER PUBLICATIONS

Hintermann et al. The Biological Stability of Beta–Peptides . . . Chimia. May 1997, vol. 50, No. 5, pp. 244–247.*

Seebach et al. Biological and Pharmacokinetic Studies with Beta–Peptides, Chimia. Dec. 1998, vol. 52, No. 12, pp. 734–739.*

(List continued on next page.)

Primary Examiner—Jeffrey E. Russel
(74) Attorney, Agent, or Firm—Swidler Berlin Shereff Friedman, LLP

(57) ABSTRACT

An antibacterial β-peptide having the following formula:

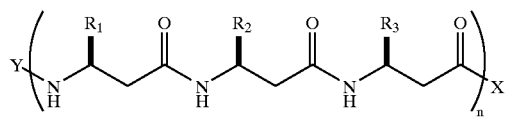

wherein
  $R_1$ is H, an alkyl group including 1–4 carbon atoms, phenyl, heteroaryl, or an alkyl-aryl;
  $R_2$ is an amine-containing alkyl group having the formula —$(CH_2)_m NH_2$, wherein m=1, 2, 3, 4, or 5, $(CH_2)_x NHC=NHNH_2$ wherein x is 1, 2, 3, 4, or 5, a pyridyl, an alkylpryidyl, an amidine-substituted benzyl, a phenyl group, or a cyclic amidine;
  $R_3$ is H, an alkyl group including 1–4 carbon atoms, phenyl, heteroaryl, or an alkyl-aryl;
  X is —$NH_2$, —OH, —NHR, or OR where R is alkyl, aryl or acyl groups either free or polymer-supported, a carboxamide, a substituted carboxamide, or a polymer;
  Y is H, an alkyl group, an acyl group, an acyl-terminated polymer, a sulphonamide, an ether, a urea, a urethane, or a polymer; and
  n is 2, 3, 4, 5, 6, or 7.

20 Claims, 6 Drawing Sheets

OTHER PUBLICATIONS

Hamuro et al. De Novo Design Of Antibacterial Beta-Peptides. J. Am. Chem. Soc. 1999. vol. 121, pp. 12200–12201.*

Werder et al. Beta-Peptides As Inhibitors Of Small-Intestinal Cholesterol And Fat Absorption. Helvetica Chimica Acta. 1999. vol. 82, No. 10. pp. 1774–1783.*

Oh et al., Biochem. Biophys. Acta. 2000, 1463: 43–54.

Porter et al., NATURE, 2000, 404, 565.

Seebach et al., β–Peptides: a surprise at every turn , Chem. Commun., 1997, 2015–2022.

1999 American Chemical Society, J.Am. Chem. Soc., Hamuro ja992728p Supporting Info pp. 1–6.

* cited by examiner

DESIGN, PREPARATION, AND PROPERTIES OF ANTIBACTERIAL β-PEPTIDES

This application claims priority to provisional application No. 60/170,110 of the same title filed Dec. 10, 1999, the entire contents of the disclosure of which is hereby incorporated by reference.

This work was supported by grants from the MRSEC program of the NSF, and NSF grants 9634646 and 9905566.

FIELD OF THE INVENTION

The invention relates to β-peptides, or peptides including P-amino acids, particularly β-peptides that exhibit antibacterial properties. The present invention also relates to materials that incorporate the peptides, thereby providing the materials with antibacterial properties.

BACKGROUND OF THE INVENTION

Most proteins typically found in nature are made up of α-amino acids. In a-amino acids, the amino group is attached to the molecule at the α-carbon atom. The amino group may also be attached to other carbon atoms. For example, in β-amino acids and gamma-amino acids, the amino group may be attached to other carbon atoms.

Incorporation of different amino acid forms can result in differences in the structure of proteins that incorporate the amino acids. In a protein that incorporates β-amino acids, the amino group of the amino acid is still bonded to the carboxylic acid group of an adjacent amino acid, forming an amide bond. When β-amino acids are joined to form a protein, an extra carbon atom will be present in the chain of carbon atoms formed in the protein.

Proteins can have primary, secondary, tertiary and quaternary structures. The function of a protein may be related to its structure since the structure may permit the protein to interact with other molecules or structures. For example, having a certain sequence of amino acids that fold in a certain manner, a protein may have a complementary structure to another molecule or portion of a cell structure, thereby permitting the protein to interact with other molecules or cells. Changing the arrangement of the atoms in the amino acids, as with β-amino acids, and, subsequently, changing a protein or peptide does not alter the nature of the atoms and, for example, charges associated with the atoms.

SUMMARY OF THE INVENTION

The present invention provides particular β-peptides that have antibacterial properties. The antibacterial β-peptide can have the following formula:

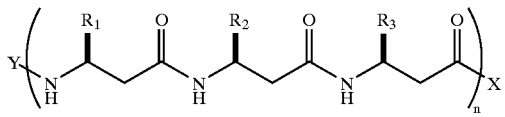

wherein
R₁ is H, an alkyl group including 1–4 carbon atoms, phenyl, heteroaryl, or an alkyl-aryl;
R₂ is an amine-containing alkyl group having the formula —(CH₂)ₘNH₂, wherein m=1, 2, 3, 4, or 5, (CH₂)ₓNHC=NHNH₂ wherein x is 1, 2, 3, 4, or 5, a pyridyl, an alkylpryidyl, an amidine-substituted benzyl, a phenyl group, or a cyclic amidine;
R₃ is H, an alkyl group including 1–4 carbon atoms, phenyl, heteroaryl, or an alkyl-aryl;
X is —NH₂, —OH, —NHR, or OR where R is alkyl, aryl or acyl groups either free or polymer-supported, a carboxamide, a substituted carboxamide, or a polymer;
Y is H, an alkyl group, an acyl group, an acyl-terminated polymer, a sulphonamide, an ether, a urea, a urethane, or a polymer; and
n is 2, 3, 4, 5, 6, or 7.

Additionally, the present invention provides antibacterial P-peptides having the following formula:

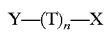

wherein
n is 2, 3, 4, 5, 6, or 7;
X is —NH₂, —OH, —NHR, or OR where R is alkyl, aryl or acyl groups either free or polymer-supported, a carboxamide, a substituted carboxamide, or a polymer;
Y is H, an alkyl group, an acyl group, an acyl-terminated polymer, a sulphonamide, an ether, a urea, a urethane, or a polymer; and
T is a triplet including T1-T2-T3, wherein T1 comprises a hydrophobic β-amino acid, T2 comprises a polar or basic amino acid, T3 comprises either a hydrophobic β-amino acid or a polar or basic β-amino acid, wherein at least one-half of the triplets include a basic β-amino acid.

Significantly, the present invention concerns a number of applications of these β-peptides to provide antibacterial properties when incorporated into other materials.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DETAILED DESCRIPTION OF THE INVENTION

Figure 1:
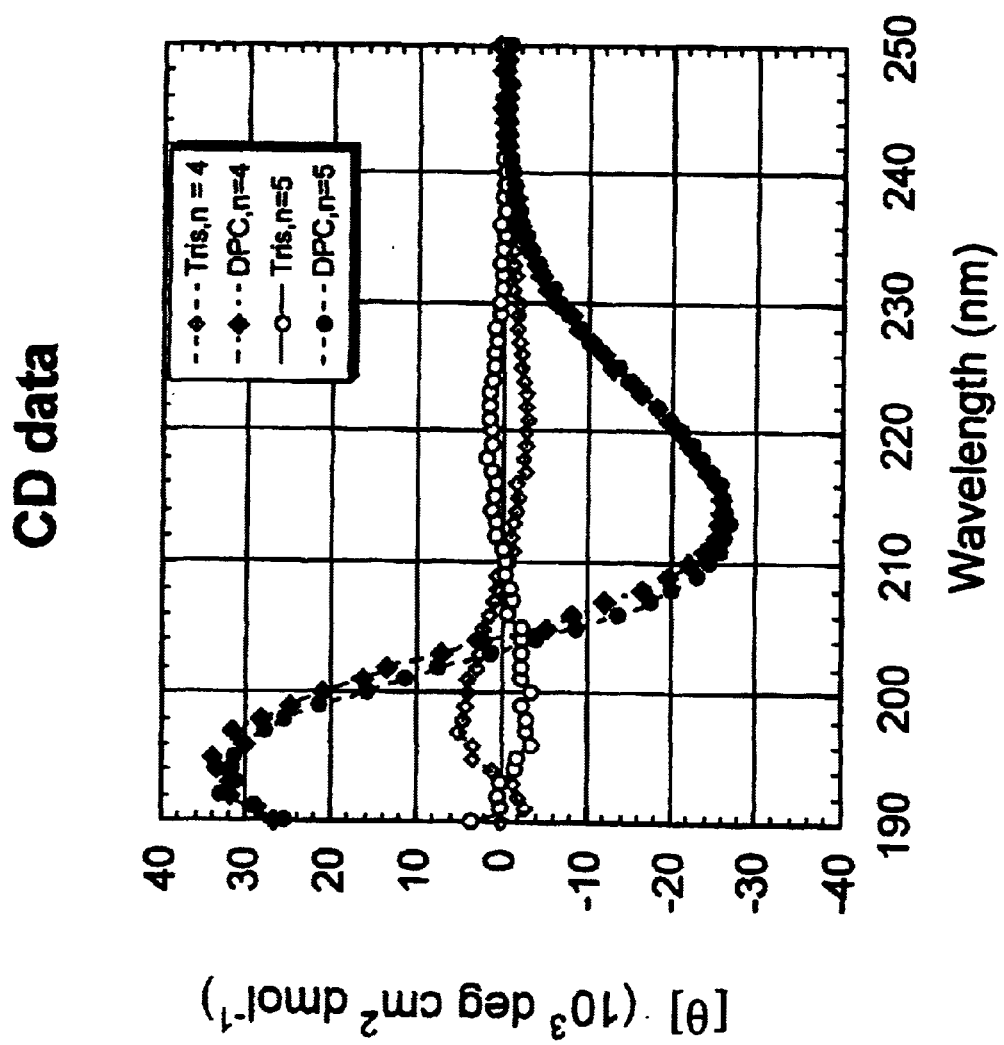
FIG. 1 represents a graph that illustrates results of circular dichroism spectroscopy studies on compounds 1 and 2 of group II of compounds according to the present invention.

Many vertebrates and invertebrates secrete natural substances that possess both antibacterial and/or indiscriminate cytotoxic properties. Examples of some of these substances include PGLa (frog skin), defensins (human phagocytes), cecropins (Silkmoth pupae or pig intestine), apidaecins (honeybee lymph), melittin (bee venom), bombinin (toad skin) and the magainins (frog skin). Purification of the active constituents of these natural substances have shown that they consist primarily of protein and it has been suggested that they may constitute a system of cellular immunity in the producing organism.

Peptides and oligopeptides that have activity against microorganisms span a broad range of molecular weights, secondary conformations and sites of action. Biological activity can range from being specifically bactericidal or fungicidal to being indiscriminately cytotoxic (cell lytic) to all cells. Peptides that are specifically bactericidal include large polypeptides such as lysozyme (MW 15000 daltons) and attacins (MW 20–23,000 daltons) as well as smaller polypeptides such as cecropin (MW 4000 daltons) and the magainins (MW 2500 daltons). The spectrum of biocidal activity of these peptides is somewhat correlated to size. In general, the large polypeptides are active against limited types and species of microorganisms (e.g., lysozyme against only gram positive bacteria), whereas many of the smaller oligopeptides demonstrate a broad spectrum of antibacterial activity, killing many species of both gram positive and gram negative bacteria.

In part, the antibacterial properties of the P-peptides may stem from the three dimensional structures that they adopt. Along these lines, it has been demonstrated that relatively short (compared with α-peptides) oligomer sequences of β-peptides derived from β-amino acids adopt well-defined helical secondary structures in both organic and aqueous solution. It should be possible to design polymers that fold not only into predetermined secondary structures, but also tertiary and quaternary structures. Unlike natural α-peptides, β-peptides have been shown to be chemically stable and resistant to enzymatic degradation, such as resistance to proteases. As a result, they seem to provide an attractive medium for the construction of biomimetic polymers.

β-peptides have been demonstrated to have remarkable properties. β-peptides can adopt secondary structures such as helices, sheets and turns, which are very similar to the counterparts of natural proteins. The substitution pattern of β-amino acids is found to be an important determining factor of the secondary structure that their oligomers form. Since β-amino acids include two backbone carbon atoms that can bear side groups, β-peptides generally have larger diversity of secondary structures than natural peptides.

The natural antimicrobial peptides that have been isolated from defense systems of insects, amphibians and mammals have exhibited activity against large varieties of bacteria, fungi, and even tumor cells. A number of studies have been carried out on their structure activity relationship, especially the structural class of amphipathic linear peptides. A number of studies have been carried out on their structure activity relation (SAR), especially the family of amphipathic linear peptides. Usually peptides of this type have multiple positive charges from residues such as lysine and arginine. In aqueous solution, these peptides often adopt a random coil structure but they form amphiphilic β-helical structures when they interact with phospholipid bilayers of cellular membranes. It is believed that this interaction results in a disruption of the cell membrane causes the cell death. The factors that influence their selective antibacterial activities include hydrophobicity, charge distribution, helical propensity and length of the peptide. Generally, the more hydrophobic the peptide, the less selective it is. For peptides that have certain hydrophobicity and charge distribution patterns, optimum selectivity can be reached at a critical length.

These discoveries in part led to the present invention. Particularly relevant were the discoveries related to the folding of the proteins. At least in part, a periodicity to hydrophobic residues included in the proteins seems to be particularly important to their folding and subsequent antibacterial properties.

In general, peptides according to the present invention include multiples of groups of three β-amino acids. Typically, the peptides include at least two multiples of the groups of three β-amino acids, or also referred to as triads or triplets herein. As many as 7 multiples may be included. At least as many multiples as are necessary to make one turn of a helix structure typically are included.

It is not necessary that each triplet be the same. Each triplet of β-amino acids may be different. One factor that may be significant in determining which β-amino acids to include in each group is the nature of the groups. In other words, the hydrophobicity, hydrophilicity, polarity, or other characteristics may be important. This is especially true in considering how the peptide will fold in the final molecule and whether the desired arrangement will result from the selected amino acids. Typically, the peptides of the present invention form a L+2 helix. As discussed herein, molecules may be constructed to have structures that take on this helical configuration in relevant conditions.

In one embodiment, each triplet of β-amino acids includes a hydrophobic β-amino acid on each end with a β-amino acid having a polar side chain in the middle. However, as stated above, each group of three amino acids need not be the same. In some cases, it is sufficient for at least one-half of the β-amino acids to be a basic β-amino acid.

Typically, the β-amino acids that are utilized in the present invention include alanine, valine, leucine, and lysine. However, substitutions may be made on these amino acids, at any carbon atom, but particularly at the second and third carbon atoms, the carbon atoms adjacent where the carboxylic acid group is present and the next carbon atom down the molecule.

A number of groups may be attached to the ends of the peptide. Along these lines, the peptide may terminate in the carboxylic acid and amine groups. However, more typically, additional groups may be attached to the peptide. A number of groups are listed below. However, a significant aspect of the present invention is that the peptides can be incorporated into a number of products that can take advantage of the antibacterial properties that have been discovered for these peptides. Along these lines, the peptides according to the present invention could be incorporated into materials for making surfaces, fibers and films. Examples could include medical devices, such as catheters, endotracheal tubes, scalpel handles, implants, such as hip replacements, knee replacements, or any other medically related product. Additional examples include countertops, cutting boards, sponges, packaging materials, wipes, and any number of other articles or mateirals where antibacterial functionality is desired.

A few examples of polymers that the peptides according to the present invention are attached to include polyurethane, polyetherurethane, polyester, silicone, polyamide, polyolefin, polystyrene, polypeptide, polysaccharide, cellulosic, and silk. The peptides of the present invention may be linked to the polymer by a non-cleavable linker. Examples of such linkers, as well as polymers and attaching peptides to polymers are provided by U.S. Pat. No. 5,847,047, to Haynie, the entire contents of the disclosure of which is hereby incorporated by reference.

The β-peptides according to the present invention may also be non-covelently bonded to a carrier. The linking to a carrier may be for the purpose of facilitating use of a peptide. For example, a peptide could be combined with a material that could be dried and made into a powder. This powder could then be applied to a countertop material to provide antibacterial functionality to the countertop. An example of a carrier is sol-gel derived silica glass material.

The peptides according to the present invention could also be used as part of an antibacterial composition. Along these lines, the peptides could be incorporated into a solution, foam, or other agent that could be used to apply to surfaces for disinfecting purposes. The peptides could also be utilized with a suitable vehicle or carrier as part of a pharmaceutical composition. Such a composition could be applied topically or otherwise.

The present invention provides an antibacterial β-peptide having the following formula:

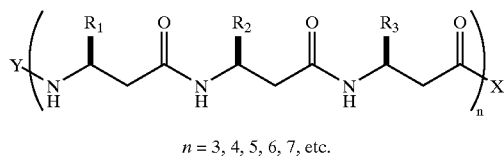

$n = 3, 4, 5, 6, 7,$ etc.

wherein $R_1$ is H, an alkyl group including 1–4 carbon atoms, phenyl, heteroaryl, or an alkyl-aryl;

$R_2$ is an amine-containing alkyl group having the formula —$(CH_2)_m NH_2$, wherein m=1, 2, 3, 4, or 5, $(CH_2)_x$ NHC=NHNH$_2$ wherein x is 1, 2, 3, 4, or 5, a pyridyl, an alkylpryidyl, an amidine-substituted benzyl, a phenyl group, $CH_2$-imidazole, $CH_2$-indole or a cyclic amidine;

$R_3$ is H, an alkyl group including 1–4 carbon atoms, phenyl, heteroaryl, or an alkyl-aryl;

X is —$NH_2$, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and n is 2, 3, 4, 5, 6, or 7.

While the alkyl groups of $R_1$ and $R_3$ may be any alkyl group, specific examples include methyl, ethyl, n-propyl, i-prop, n-butyl, sec-butyl, or tert-butyl.

The present invention also provides an antibacterial P-peptide having the following formula:

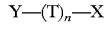

wherein n is 2, 3, 4, 5, 6, or 7;

X is —$NH_2$, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and T is a triplet or triad including T1-T2-T3, wherein T1 comprises a hydrophobic β-amino acid, T2 comprises a polar or basic amino acid, T3 comprises either a hydrophobic β-amino acid or a polar or basic β-amino acid, wherein at least one-half of the triplets include a basic β-amino acid, in other words, at least one half of the T groups (each including three β-amino acids) include a basic amino acid.

Each triplet need not be the same. A peptide could be a homopolymer of triplets each having the same pattern. Alternatively, a peptide could be a copolymer of repeating patterns of different triplets. For example, two triplets having different amino acid sequence from each other could be repeated in the peptide. It can be seen that the peptide could include any repeating pattern of triplets.

According to another formulation, an antibacterial β-peptide has the following formula:

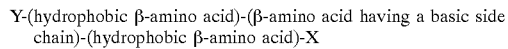

wherein

X is —$NH_2$, —OH, —NHR, or OR where R is alkyl aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer.

The β-amino acids may be substituted at at least one of the C2 and C3 atoms. The substituents may include an aryl, or a $C_{1-10}$ straight or branched, linear or cyclic alkane, alkene, or alkyne, and wherein the stereochemistry of the P-peptide is in an aldol, or anti configuration. Examples could include —H, —$CH_3$, —$CH(CH_3)_2$, —$CH_2$—$CH(CH_3)_2$, —CH($CH_3$)$CH_2CH_3$, —$CH_2$-phenyl, —$CH_2$-pOH-phenyl, —$CH_2$-indole, —$CH_2$—SH, —$CH_2$—$CH_2$—S—$CH_3$, $CH_2OH$, —CHOH—$CH_3$, —$CH_2$—$CH_2$—$CH_2$—$CH_2$—$NH_2$, —$CH_2$—$CH_2$—$CH_2$—NH—C(NH)$NH_2$, —$CH_2$-imidazole, —$CH_2$—COOH, —$CH_2$—$CH_2$—COOH, —$CH_2$—$CONH_2$, —$CH_2$—$CH_2$—$CONH_2$, or together with an adjacent —NH group forms a proline amino acid residue. Furthermore, the substiuents on the amino acids may themselves by substituted. The substituents on the substituents may be any of the above-listed substituents on the amino acids themselves.

Amino acids that are disubstituted have the following configuration:

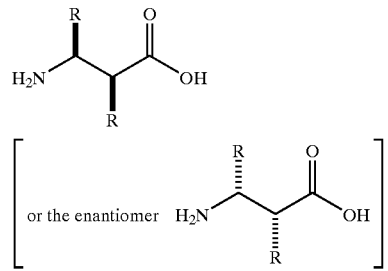

In other words, both substituents extend toward the same side of the molecule. This configuration typically generates the desired L+2 helical configuration and the desired functionality.

At least one α-amino acid or at least one β-amino acid may be arranged in the molecule between Y and T and/or X and T. If the amino acid is a β-amino acid it may be a hydrophobic, polar, or basic β-amino acid.

With either of the above two formulations, the polymers referred to in the formulas, may be any of the polymers discussed above. Similarly, peptides according to either formulation may be non-covalently bonded to a carrier such as those discussed above.

A particularly stable structure formed by β-peptides is the $L_{+2}$ helix which contains three β-amino acid residues per turn of the helix. The thermodynamic stability of such a helix may also depend upon its chain length; the longer the chain, the more thermodynamically stable it typically is. Some β-peptides according to the present invention were designed with alternating hydrophobic residues such as homo-valine or homo-leucine at the i and i+2 positions of the β-peptide with a β-amino acid at i+1 position having a positively charged amino group on the sidechain such as homo-lysine.

The following represent three examples (I, II, and III) of β-peptides according to a first group:

Fmoc-(β³-HVal-β³-HLys-β³-HLeu)$_n$-OH; n=2–4 (I)

H-(β³-HVal-β³-HLys-β³-HLeu)$_n$-OH; n=2–4 (II)

H-(β³-HLeu-β³-HLys-β³-HLeu)$_n$-OH; n=2–6 (III)

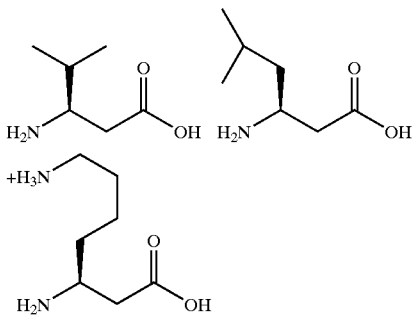

The above peptides were synthesized by solid phase peptide synthesis, using tripeptide blocks prepared on a 2,4-dialkoxy-benzyl ester polymer support as described below. The Fmoc group in the first series of peptides provided a convenient probe for determining the concentration of the peptides. To determine the effect of this hydrophobic probe on the properties of the compounds, a parallel series of peptides was synthesized without this group.

The ability of these peptides to adopt a L+2 helix in aqueous solution in the presence and absence of micelles and phospholipid bilayers was assessed using CD spectroscopy, which provides a rapid method to assess the secondary structure formation of p-peptides. The relationship between secondary structure formation and the CD spectra of peptides composed of cyclic β-amino acids is not yet fully developed. However, numerous studies with β-peptides assembled from the acyclic building blocks used in this work have demonstrated that the L+2 conformation gives rise to a strong minimum at 215 nm and a maximum at 195 nm in the π–π* region. The CD spectra of Fmoc-(β³-HVal-β³-HLys-β³-HLeu)$_n$-OH (n=2–4) in aqueous solution failed to exhibit these features associated with the L+2 helical conformation. This finding is consistent with previous studies showing that complete formation of the L+2 conformation by β-peptides of this length requires the addition of organic solvents and/or conformationally constrained amino acids. However, the addition of dodecyl phosphocholine (DPC) micelles resulted in a length-dependent increase in the magnitude of $[\theta]_{215\ nm}$, reaching an intensity consistent with essentially complete helix formation at n=4. Similar data were observed with small, unilamellar vesicles composed of POPC (not shown). Hydrophobic/water interfaces are similarly able to induce α-helix formation in a variety of amphiphilic α-peptides.

The presence of the hydrophobic Fmoc group appears to favor binding to DPC micelles (and concomitant formation of an L+2 helical conformation), based on the slightly greater negative ellipticity at 215 nm observed for Fmoc-(β3-HVal-β³-HLys-β³-HLeu)$_3$-OH versus H-(β³-HVal-β³-HLys-β³-HLeu)$_3$-OH. The dependence of amino acid composition on L+2 helix formation was probed by comparing the CD spectra of H-(β³-HVal-β³-HLys-β³-HLeu)$_3$-OH versus H-(β³-HLeu-β³-HLys-β³-HLeu)$_3$-OH. These spectra indicate that the β³-HVal-containing β-peptide has a slightly greater propensity to form the L+2 helix than the β³-HLeu-containing peptide. However, at chain lengths of 12 residues (n=4) or longer, helix formation appeared to be complete for all three series of peptides, because further chain elongation failed to increase the intensity of $[\theta]_{215\ nm}$.

The biological activities of these peptides were measured using human erythrocytes and E. coli as models for mammalian and bacterial cells, respectively. Hemolysis was monitored in 10 mM Tris, 150 mM NaCl, pH 7.0, while the bacterial assay was conducted in minimal media M9 (Table 1); both of these solutions are sufficiently transparent to allow CD and ultracentrifugation measurements (supplementary material). Under the assay conditions, the peptides gave CD spectra similar to those in Tris buffer, with the exception of H-(β³-HLeu-β³-HLys-β³-HLeu)$_n$-OH, n=5 and 6. Analytical ultracentrifugation indicated that these two peptides formed large aggregates in the presence of phosphate (an essential component of minimal media).

All three series of peptides show length-dependent anti-bacterial activities, which correlates with their helical contents in DPC micelles. In DPC micelles the helical content of the three 9-residue β-peptides follow the progression Fmoc-(β³-HVal-β³-HLys-β³-HLeu)$_3$-OH>H-(β³-HVal-β³-HLys-β³-HLeu)$_3$-OH>H-(β³-HLeu-β³-HLys-β³-HLeu)$_3$-OH. Approximately the same trend is observed in the biological data. However, the biological activities of the peptides continue to increase as their chain lengths are increased beyond the threshold required for complete helix formation in DPC micelles. This result may reflect the fact that longer helices have a higher surface area available for binding to membrane surfaces, providing enhanced affinity and greater efficacy.

Below are two more examples (IV and V) of the first group of peptides. These are particular examples of the molecules shown above, with particular ranges for n.

(IV)

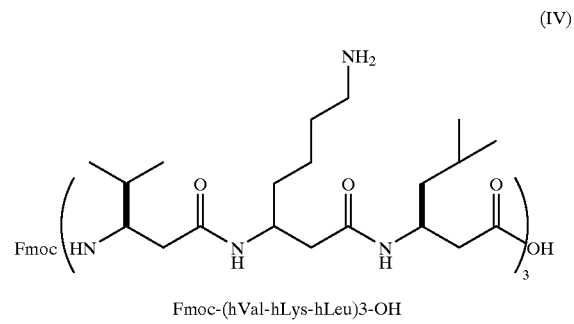

Fmoc-(hVal-hLys-hLeu)3-OH

-continued

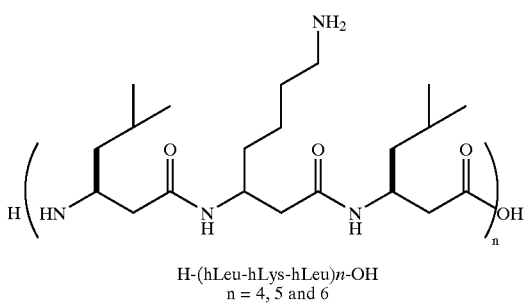

(V)

H-(hLeu-hLys-hLeu)$n$-OH
n = 4, 5 and 6

β-amino acids IV and V were prepared using the Arndt-Eistert homologation of N-Fmoc α-amino acids as described by Seebach as described in International Patent Document WO 97/47593 to Seebach, the entire contents of the disclosure of which are hereby incorporated by reference, and peptides were prepared via solid-phase peptide synthesis (Fmoc chemistry) in tripeptide blocks. The peptides greater than 6 residues (2 turns of the $L_{+2}$ helix) were found to have length-dependent antibacterial activities T$\mu$M levels) against E. coli. These molecules also exhibit hemolytic activity against human red blood cells.

Stress-induced response and growth inhibition assays were carried out on samples of four of the β-peptide and compared to known polycationic peptides. The results are listed in Table 1.

TABLE 1

Stress Response and Growth Inhibition Results of β-peptides

| natural peptides | osmY-lux | micF-lux | MIC* ($\mu$M) |
|---|---|---|---|
| Polymyxin B | + | + | 0.2 |
| Polymyxin E | + | + | 0.15 |
| Cecropin A | + | + | 0.1 |
| Cecropin B | + | + | 0.1 |
| Magainin 1 | + | − | 12 |
| Magainin 2 | + | − | 5 |

| β-peptides | ≈IC$_{50}$ of recA-lux inhibition # ($\mu$M) | IC$_{50}$ ($\mu$M) | HD50+ | HD50/ IC50 |
|---|---|---|---|---|
| Fmoc-(hVal-hLys-hLeu)$_3$-OH | − | 16 | 15 | 6.3 | 0.42 |
| H-(hLeu-hLys-hLeu)$_4$-OH | − | − | 64 | 1.7 | 2.6 | 1.5 |
| H-(hLeu-hLys-hLeu)$_5$-OH | + | − | 24 | ND | 0.23 |
| H-(hLeu-hLys-hLeu)$_6$-OH | − | − | 2 | ND | 0.081 |

Polymyxin B was tested both rich, LB, medium and defined, M9, medium. The other natural peptides were tested in LB medium.
The β-peptides were tested in M9 medium. * In LB medium (data from Oh et al. Biochem. Biophys. Acta. 2000,1463: 43–54)
∇in M9 medium (data from Hamuro et al., ref. 5) # In M9 medium.+Hemolysis experiments were performed by incubating a 0.25% suspension of human RBc's in 10 mM Tris buffer containing 150 nM NaCl at pH 7.0 with varying amounts of peptide. The hemolytic dose required to lyse 50% of the RBC's is reported as the HD$_{50}$.

With the exception of H-(hLeu-hLys-hLeu)$_5$-OH, the β-peptides did not induce the osmY-lux fusion, an observed induction for polycationic amphiphilic antibacterial α-peptides such as the magainins. However, similar to the magainins, no induction of the micF-lux fusion was observed. Also, the minimum inhibitory concentrations (MIC's) were determined to be higher than those reported in the published manuscript. Results from these assays can aid in understanding of the genetic profile of antibacterial activities displayed by these and other β-peptides.

Table 2 below provides selected data regarding the β-peptides of group 1.

TABLE 2

| Peptide | Hemolysis[a] HD50 ($\mu$M) | Antibacterial assay[b] IC50 ($\mu$M) | Selectivity HD50/IC50 |
|---|---|---|---|
| Fmoc-(β$^3$-HVal-β$^3$-HLys-β$^3$-HLeu)$_2$-OH | >100 | >100 | — |
| Fmoc-(β$^3$-HVal-β$^3$-HLys-β$^3$-HLeu)$_3$-OH | 6.3 | 15 | 0.42 |
| Fmoc-(β$^3$-HVal-β$^3$-HLys-β$^3$-HLeu)$_4$-OH | 0.31 | 1.5 | 0.21 |
| H-(β$^3$-HVal-β$^3$-HLys-β$^3$-HLeu)$_2$-OH | >100 | >100 | — |
| H-(β$^3$-HVal-β$^3$-HLys-β$^3$-HLeu)$_3$-OH | 86 | 41 | 2.1 |
| H-(β$^3$-HVal-β$^3$-HLys-β$^3$-HLeu)$_4$-OH | 4.2 | 2.1 | 2.0 |
| H-(β$^3$-HLeu-β$^3$-HLys-β$^3$-HLeu)$_2$-OH | >100 | >100 | — |
| H-(β$^3$-HLeu-β$^3$-HLys-β$^3$-HLeu)$_3$-OH | >100 | 35 | >2.9 |
| H-(β$^3$-HLeu-β$^3$-HLys-β$^3$-HLeu)$_4$-OH | 2.6 | 1.7 | 1.5 |
| H-(β$^3$-HLeu-β$^3$-HLys-β$^3$-HLeu)$_5$-OH | 0.23 | — | — |
| H-(β$^3$-HLeu-β$^3$-HLys-β$^3$-HLeu)$_6$-OH | 0.081 | — | — |

[a]Hemolysis experiments were performed by incubating a 0.25% suspension of human erythrocytes (RBC's) in 10 mM Tris buffer containing 150 mM NaCl at pH 7.0 with varying amounts of peptide. After 1 h at 37° C., the suspensions were centrifuged and the OD$_{414 \text{ nm}}$ of the supernatant (due to released hemoglobin) was measured. The hemolytic dose required to lyse 50% of the RBC's was obtained as described in the Supplementary Material.
[b]Antibacterial assays were performed by incubating varying amounts of peptide with cultures of K91 E. Coli in minimal media at pH 7.4. After 9 h at 37° C., the OD$_{600 \text{ nm}}$ of the culture was measured (light scattering due to bacteria). The peptide dose required to supress 50% bacterial growth was obtained as described herein.

(a) Synthesis of Fmoc-β$^3$-HXxx-β$^3$-HLys(Boc)-β$^3$-HLeu-OH. The protected peptide fragments were assembled by using super acid labile HMPB-MBHA resin (Scheme 1). First, Fmoc-β$^3$-HLeu-OH was attached onto the resin by DIC-DMAP protocol followed by pivaloyl anhydride capping. A standard Fmoc solid phase peptide synthesis, deprotection of Fmoc group by piperidine and coupling with Fmoc-β-amino acids with HBTU-HOBt, gave the tripeptides on the resin, which were then treated with 1% TFA in dichloromethane to give the desired protected β-peptide fragments in (HXxx=HVal, 56%; HXxx=HLeu, 86%). The crude peptide fragments were used for the segment condensation without further purification.

Scheme 1

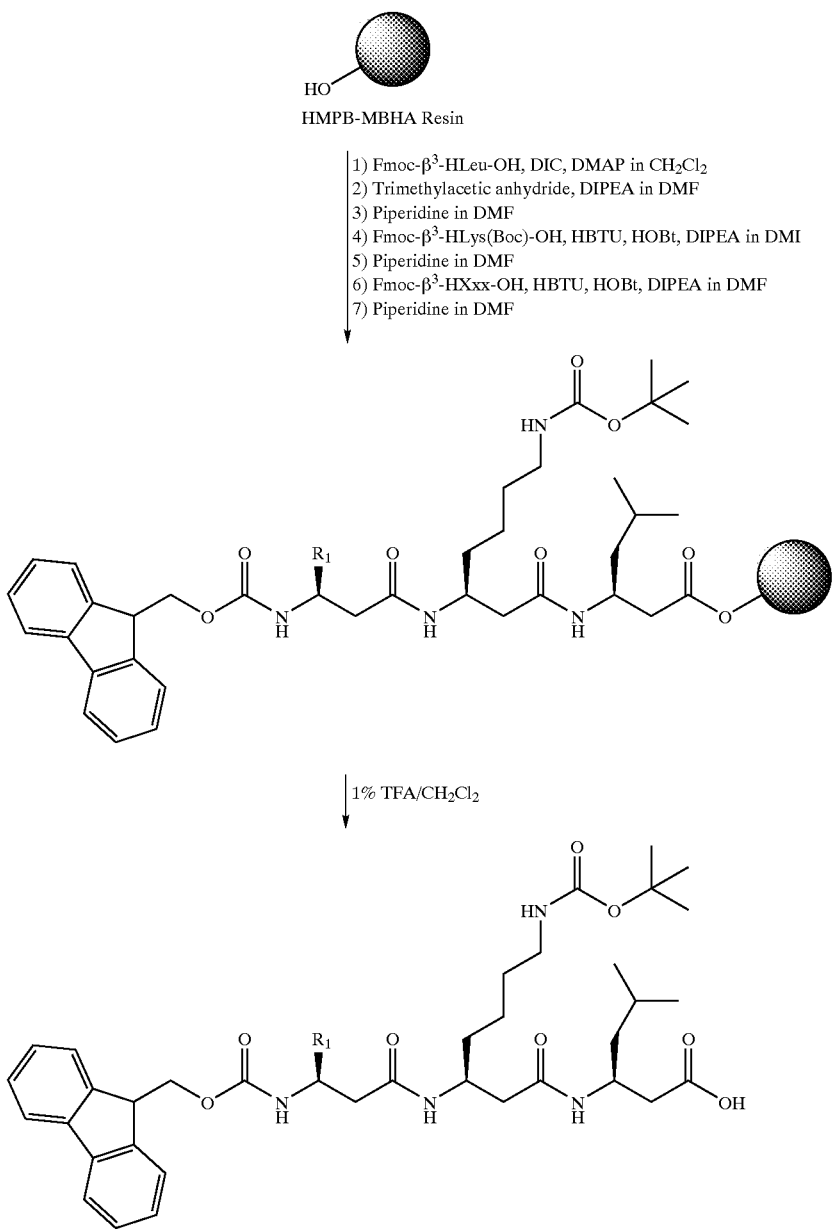

(b) Synthesis of Fmoc-(β³-HValβ³-HLys-β³-HLeu)$_n$-OH (n=2–4) and H-(β³-HLeu-β³-HLys-β³-HLeu)$_n$-OH (n=2–6). The titled β-peptides were synthesized from protected tripeptide fragment, Fmoc-β³-HXxx-β³-HLys(Boc)-β³-HLeu-OH (HXxx=HVal or HLeu), using Wang resin and standard Fmoc protocol (Scheme 2). The first fragment was attached onto Wang resin by DIC-DMAP protocol and the unreacted hydroxyl group on the resin was capped by the treatment with a solution of benzoyl chloride and pyridine. The reiterative piperidine deprotections and HBUT-HOBt couplings gave the β-peptides on Wang resin. TFA cleavage and HPLC purification yielded the titled β-peptides.

Scheme 2

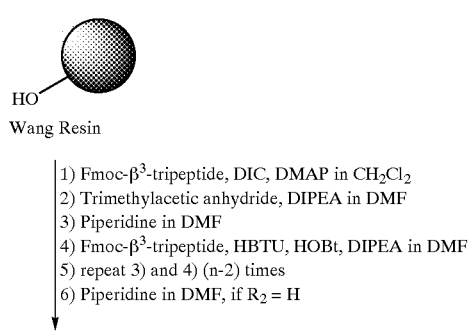

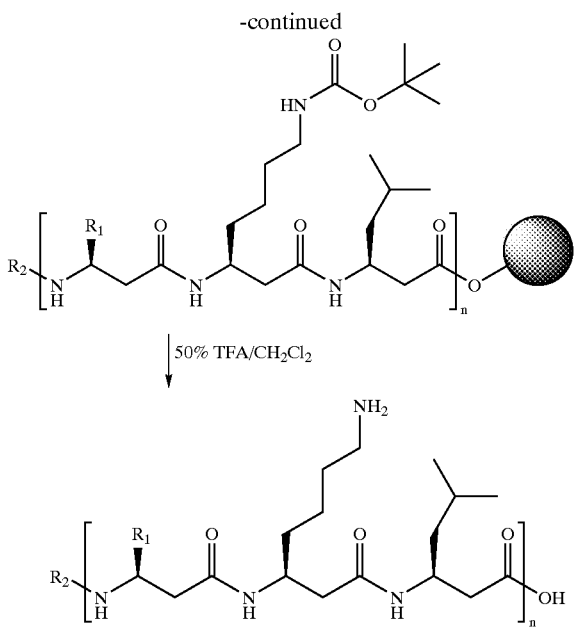

The following describes the synthesis of β-peptides of the Group I. Fmoc-(b³-HVal-b³-HLys-b³-HLeu)$_n$-OH (n=2–4) and Fmoc-(b³-HLeu-b³-HLys-b³-HLeu)$_n$-OH (n=2–6) were prepared by segment condensation from the fully protected tripeptide fragments Fmoc-(b³-HVal-b³-HLys(Boc)-b³-HLeu)-OH and Fmoc-(b³-HLeu-b³-HLys(Boc)-b³-HLeu)-OH, respectively. The initial tripeptide fragment was coupled to Wang resin employing diisopropylcarbodiimide (DIC)/4-dimethylaminopyridine (DMAP) activation. Subsequent tripeptide fragments were added sequentially after terminal Fmoc-deprotection (20% piperidine in N,N-dimethylformamide (DMF)) employing 2-(1H-benzotriazole-1-yl)-1,1,3,3-tetramethyluronium hexafluorophosphate (HBTU)/1-Hydroxybenzotriazole (HOBt) activation. The resin bound peptides were cleaved and side-chain deprotected (50% trifluoroacetic acid (TFA) in CH$_2$Cl$_2$).

The peptides H-(b³-HVal-b³-HLys-b³-HLeu)$_n$-OH (n=2–4) and H-(b³-HLeu-b³-HLys-b³-HLeu)$_n$-OH (n=2–6) were prepared by N-terminal Fmoc-deprotection (20% piperidine in DMF) of Fmoc-(b³-HVal-b³-HLys-b³-HLeu)$_n$-OH (n=2–4) and Fmoc-(b³-HLeu-b³-HLys-b³-HLeu)$_n$-OH (n 2–6).

Tripeptide fragments Fmoc-(b³-HVal-b³-HLys(Boc)-b³-HLeu)-OH and Fmoc-(b³-HLeu-b³-HLys(Boc)-b³-HLeu)-OH were prepared on super acid labile HMPB-MBHA resin by standard Fmoc solid phase peptide synthesis protocol employing HBTU/HOBt activation. Treatment of the resin-bound peptide with 1% TFA in CH$_2$Cl$_2$ afforded fully protected crude tripeptide which was used for segment condensations without further purification.

The appropriate Fmoc-protected b-amino acid residues used to synthesize the tripeptide fragments were prepared from the corresponding Fmoc-a-amino acids by Arndt-Eistert homologation following the procedure disclosed by Atherton, E.; Sheppard, R. C. In *The Peptides*; Udenfriend, S., Meienhofer, J., Ed.; Academic Press: Orland, Fla., 1987; Vol. 9; pp 1–38, the entire contents of the disclosure of which is hereby incorporated by reference. The synthesis of all tripeptide fragments and full length peptides are outlined below.

Fmoc-a-amino acids were purchased from Bachem Bioscience Inc., HBTU from Advanced ChemTech., and all other reagents from Aldrich and were used without further purification. HMPB-MBHA (loading=0.51 mmol/g) and Wang (loading=0.85 mmol/g) resins were purchased from Novabiochem. Peptides were synthesized in standard glass peptide synthesis vessels. Nominal mass determinations were carried out by electrospray ionization (ESI) employing a Hewlett-Packard 1100 coupled to a Micromass Platform LC. High resolution mass spectra were obtained with a Micromass AutoSpec ESI mass spectrometer. UV measurements were performed with a Hewlett-Packard 8453 spectrometer. Peptides were purified using a preparative Vydac C4 peptide/protein column. Solvent A was composed of water and 0.1% TFA and solvent B was composed of 90% acetonitrile, 10% water and 0.1% TFA, unless noted otherwise. Peptide purity was accessed by analytical HPLC analyses employing a HP-1100 liquid chromatography system equipped with a photodiode array detector and a Vydac C4 column (2.1×150 mm).

General Procedure for the synthesis of tripeptide fragments Fmoc-(b³-HVal-b³-HLys(Boc)-b³-HLeu)-OH and Fmoc-(b³-HLeu-b³-HLys(Boc)-b³-HLeu)-OH. HMPB-MBHA resin (5.0 g, 2.55 mmol) was added to a solution of Fmoc-b³-HLeu-OH (1.10 g, 3.0 mmol), DIC (470 mL, 3.0 mmol) and DMAP (0.37 g, 3.0 mmol) in CH$_2$Cl$_2$ (50 mL) and the reaction mixture was left at room temperature for 40 h. The resin was then washed with DMF (4×1 min). Unreacted resin was capped with a solution of trimethylacetic anhydride (5.2 mL, 25.5 mmol) and pyridine (2.06 mL, 25.5 mmol) in DMF (40 ML) for 1 h and the resin subsequently washed with DMF (5×1 min). The following cycle was used to couple subsequent Fmoc-protected amino acids: Fmoc-deprotection (20% piperidine in DMF for 1 h), DMF wash (5×1 min), coupling (2.8 mmol of Fmoc-b-amino acid, 1.06 g (2.8 mmol) of HBTU, 0.43 g (2.8 mmol) of HOBt, 0.98 mL (5.6 mmol) of diisopropylethylamine (DIEA) in DMF (40 mL) for 40 h), DMF wash (5×1 min).

After the final coupling, the resin was washed with DMF (5×1 min), MeOH (4×1 min), CH$_2$Cl$_2$ (4×1 min) and dried. The resin-bound tripeptide was cleaved with 1% TFA in CH$_2$Cl$_2$ (50 mL×8 min, 50 mL×2 min×4). Each filtrate was directly introduced into 2% pyridine in MeOH (50 mL). The resin was washed with CH$_2$Cl$_2$ (3×50 mL×5 min) and MeOH (3×50 mL×5 min). All filtrates were combined and the volume reduced by evaporation in vacuo to a final weight of 60 g. Water (150 mL) was then added to precipitate the desired fully protected tripeptide which was collected by filtration and dried under high vacuum affording product as a white powder. Crude peptide fragments were used for segment condensations without further purification.

Fmoc-b³-HVal-b³-HLys(Boc)-b³-HLeu-OH. White solid (593 mg, 56%): HRMS (ESI) m/e calcd for C$_{40}$H58N$_4$O$_8$Na (M+Na⁺) 745.4152, found 745.4136.

Fmoc-b³-HLeu-b³-HLys(Boc)-b³-HLeu-OH. White solid (1.61 g, 86%): HRMS (ESI) m/e calcd for C$_{41}$H$_{60}$N$_4$O$_8$Na (M+Na⁺) 759.4309, found 759.4335.

General Procedure for the synthesis Fmoc-(b³-HVal-b³-HLys-b³-HLeu)$_n$-OH (n=2–4). Wang resin (0.88 g, 0.75 mmol) was added to a suspension of Fmoc-(b³-HVal-b³-HLys(Boc)-b³-HLeu)-OH (0.5 mmol), DIC (78 mL, 0.5 mmol) and DMAP (0.06 g, 0.5 mmol) in CH$_2$Cl$_2$ (15 mL) and the reaction mixture was left at room temperature for 48 h. The resin was then washed with CH$_2$Cl$_2$ (4×1 min), DMF (4×1 min), MeOH (4×1 min), CH$_2$Cl$_2$ (4×1 min). Unreacted resin was capped with a solution of trimethylacetic anhydride (0.5 mL, 2.5 mmol) and pyridine (0.2 mL, 2.5 mmol) in DMF (10 mL) for 2 h and the resin subsequently washed with DMF (5×1 min). The following cycle was used to couple subsequent tripeptide fragments (aliquots of resin-bound peptide were removed after each coupling step to obtain resin-bound peptides of appropriate length): Fmoc-deprotection (20% piperidine in DMF for 1 h), DMF wash (4×1 min), MeOH wash (4×1 min), $CH_2Cl_2$ wash (4×1 min), coupling (1.2-fold excess of tripeptide, HBTU, HOBt, and two-fold excess of diisopropylethylamine (DIEA) in DMF for 10 h), DMF wash (4×1 min), MeOH wash (4×1 min), $CH_2Cl_2$ wash (4×1 min). After the final coupling, the resin was washed with DMF (5×1 min), MeOH (4×1 min), $CH_2Cl_2$ (4×1 min) and dried. The resin-bound peptide was cleaved and side-chain deprotected with 50% TFA in $CH_2Cl_2$ for 1 h and the resin washed with $CH_2Cl_2$ (3×25 mL). The combined filtrates were evaporated affording an oil which was triturated with cold diethyl ether yielding crude Fmoc-($b^3$-HVal-$b^3$-HLys-$b^3$-HLeu)$_n$-OH (n=2–4) which was subsequently purified by HPLC.

Fmoc-($b^3$-HVal-$b^3$-HLys-$b^3$-HLeu)2-OH. Purification by preparative HPLC employing a linear gradient from 30% to 60% solvent B over 60 min. HRMS (ESI) m/e calcd for $C_{55}H_{89}N_8O_9$ (M+H$^+$) 1005.6753, found 1005.6748.

Fmoc-($b^3$-HVal-$b^3$-HLys-$b^3$-HLeu)$_3$-OH. Purification by preparative HPLC employing a linear gradient from 50% to 80% solvent B over 60 min. HRMS (ESI) m/e calcd for $C_{75}H_{127}N_{12}O_{12}$ (M+H$^+$) 1387.9696, found 1387.9853.

Fmoc-($b^3$-HVal-$b^3$-HLys-$b^3$-HLeu)4-OH. Purification by preparative HPLC employing a linear gradient from 60% to 75% solvent B over 60 min.(solvent B is composed of 60% acetonitrile, 30% isopropyl alcohol, 10% water and 0.1% TFA). FIRMS (ESI) m/e calcd for $C_{95}H_{165}N_{16}O_{15}$ (M+H$^+$) 1770.2640, found 1770.2777.

General Procedure for the synthesis H-($b^3$-HVal-$b^3$-HLys-$b^3$-HLeu)$_n$-OH (n=2–4). An eppendorf tube was charged with 2 mg Fmoc-($b^3$-HVal-$b^3$-HLys-$b^3$-HLeu)$_n$-OH and 0.25 mL of 20% piperidine in DMF. After 30 min., the solution was evaporated in vacuo yielding an oil. The oil was then triturated with cold diethyl ether affording a white solid which was collected by filtration, washed with cold diethyl ether (3×1 mL) and dried.

H-($b^3$-HVal-$b^3$-HLys-$b^3$-HLeu)2-OH. LRMS (MALDI-TOF) m/e calcd for $C_{40}H_{80}N_8O_7$ (M+H$^+$) 784.61, found 784.28.

H-($b^3$-HVal-$b^3$-HLys-$b^3$-HLeu)3-OH. LRMS (MALDI-TOF) m/e calcd for $C_{60}H_{118}N_{12}O_{10}$(M+H$^+$) 1166.9, found 1167.2.

H-($b^3$-HVal-$b^3$-HLys-$b^3$-HLeu)4-OH. LRMS (MALDI-TOF) m/e calcd for $C_{80}H_{156}N_{16}O_{13}$ (M+H$^+$) 1549.2, found 1549.6.

General Procedure for the synthesis H-($b^3$-HLeu-$b^3$-HLys-$b^3$-HLeu)$_n$-OH (n=2–6). These peptides were synthesized in a similar manner as described above with the exception that the N-terminally Fmoc-protected peptides (Fmoc-($b^3$-HLeu-$b^3$-HLys-$b^3$-HLeu)$_n$-OH) were not purified prior to the final Fmoc-deprotection step. Purification and mass spectral data of the titled peptides are as follows:

H-($b^3$-HLeu-$b^3$-HLys-$b^3$-HLeu)$_2$-OH. Purification by preparative HPLC employing a linear gradient from 20% to 50% solvent B over 60 min. HRMS (ESI) m/e calcd for $C_{42}H_{82}N_8O_7$ (M+H$^+$) 811.6385, found 811.6345.

H-($b^3$-HLeu-$b^3$-HLys-$b^3$-HLeu)$_3$-OH. Purification by preparative HPLC employing a linear gradient from 30% to 60% solvent B over 60 min. LRMS (ESI) m/e calcd for $C_{63}H_{123}N_{12}O_{10}$ (M+H$^+$) 1208.0010, found 1208.0.

H-($b^3$-HLeu-$b^3$-HLys-$b^3$-HLeu)$_4$-OH. Purification by preparative HPLC employing a linear gradient from 40% to 70% solvent B over 60 min. LRMS (ESI) m/e calcd for $C_{84}H_{163}N_{16}O_{13}$ (M+H$^+$) 1604.2586, found 1604.2666.

H-($b^3$-HLeu-$b^3$-HLys-$b^3$-HLeu)5-OH. Purification by preparative HPLC employing a linear gradient from 45% to 75% solvent B over 60 min. LRMS (ESI) m/e calcd for $C_{105}H_{202}N_{20}O_{16}$ (M) 1999.6, found 1001.3 (M+2$^{H+}$), 668.2 (M+3H$^+$), 501.5 (M+4H$^+$).

H-($b^3$-HLeu-$b^3$-HLys-$b^3$-HLeu)6-OH. Purification by preparative HPLC employing a linear gradient from 50% to 80% solvent B over 60 min. LRMS (ESI) m/e calcd for $C_{126}H_{242}N_{24}O_{19}$ (M) 2396.0, found 1199.6 (M+2H$^+$), 800.3 (M+3H$^+$), 600.6 (M+4H$^+$).

Circular Dichroism spectra were obtained on an AVIV 62DS spectropolarimeter using 1 mm quartz cells. Samples were prepared from stock solutions in either water or 50 mM Tris buffer (pH 7) and diluted to the desired concentration with the appropriate buffer or buffer containing lipid. Peptide concentrations were determined from dry weight using freshly lyophilized samples. Molecular weights were calculated, assuming that the peptides bound one TFA counterion per amine. The concentration was also determined for Fmoc-containing peptides from the absorbance of the fluorenyl group. Good (within ±10%) agreement was observed between the two methods. All spectra are corrected for buffer contributions and are reported in units of mean residue ellipticity. The CD spectra revealed that the peptides form L+2 helices when they bind to micelle and bilayer surfaces. The formation of this structure correlates with their hemolytic and antibacterial activities.

The amphiphilic β-peptides of Group I are highly active against $E.$ $coli$ as well as red cells. The potency of the longest peptide (80 nM) is considerably greater than that of melittin, whose LD$_{50}$ is approximately 0.5 µM under these conditions. However, the selectivity of the current β-peptides for bacterial versus mammalian cells is low.

With the above specific antibacterial β-peptides, the large hydrophobic groups from the homo-leucine i position of the β-peptide may be responsible for the observed hemolytic activity. By comparison, with the specific antibacterial β-peptides illustrated below, the hydrophobicity at the i position of the peptide was reduced by using homo-alanine instead of homo-leucine. The formula below represents the structure of members of a second group of peptides according to the present invention, which will referred be to herein as peptides 1 and 2 of the second group. (group II).

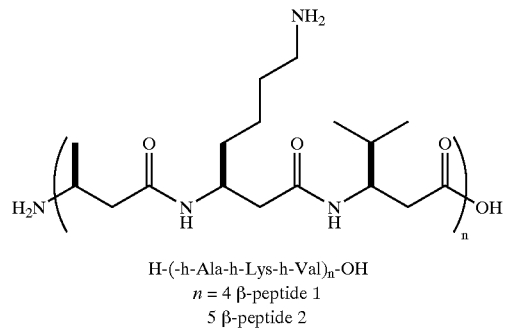

H-(-h-Ala-h-Lys-h-Val)$_n$-OH
n = 4 β-peptide 1
5 β-peptide 2

As described below in greater detail, peptides 1 and 2 both adopt L$_{+2}$ helix conformation upon binding to lipid micelle or vesicle. They have high antibacterial activity against bacteria with IC50 of several µMs, and low toxicity towards mammalian cells.

As mentioned above, for this and other proteins and peptides, circular dichoism (CD) spectroscopy is a fast and easy way to determine secondary structure. For peptides of β-amino acids, the standard of structure determination is not as well developed as it is for peptides derived from a-amino acids. Nevertheless, typical CD spectra of several types of helices adopted by β-peptides have been reported. The CD spectra of $L_{+2}$ helix have been demonstrated experimentally to have a positive cotton effect centered around 195 nm and a negative one centered around 215 nm arising from exton π–π* transition. The CD spectra of peptides 1 and 2 of Group II were measured with and without the presence of dodecyl phosphocholine (DPC) micelle. FIG. 1 illustrates the results of these tests.

In aqueous solution without lipid micelle, the CD spectra of both peptides are quite flat, suggesting random conformations. With 5 mM DPC, strong positive peak around 195 nm and negative peak around 215 nm are observed, indicating formation of $L_{+2}$ helix. The magnitudes of mean residue ellipticities of 1 and 2 are very close, suggesting the helix formation is complete at n=4. The same results are obtained with the structures above that displayed the hemolytic properties. The position of the minimum shifts slightly with the peptide length grows. The minimum of 2 is centered at 213 nm, while it is centered at 214 nm for 1. The CD data agree with the results. Without the lipid micelles, the peptides tend to be random coil because of the repulsion among positive charged homo-Lys side chains. With the presence of micelle, the hydrophobic side chains assembles to the micelle surface and the amphiphilic $L_{+2}$ helix forms.

These two β-peptides showed greater selectivity towards antibacterial activity against E coli with $IC_{50}$'s in the low micromolar range but much less hemolytic than the antibacterial β-peptides first described above. Table 3 demonstrates the properties for peptides 1 and 2 above.

TABLE 3

|  | n = 4 | n = 5 |
|---|---|---|
| $IC_{50}$ (µmol)* | 6 | 4 |
| $IC_{50}$ (µmol)# | 10 | 3 |
| $HD_{50}$ (µmol) | 670 | 240 |
| HD50/IC50 | 111 | 60 |
| induction of osmY-lux | + | + |
| induction of micF-lux | + | + |

*K91 E. coli and peptide of different concentrations in minimal media, at pH 7.4 (DeGrado lab)
inhibition of recA-lux bioluminescence in M9 media (Van Dyk lab).

Samples of these β-peptides 1 and 2 were evaluated in the stress-induced response assays. Unlike the previous antibacterial β-peptides, both showed an induction of the osm-Y and mic-F fusions similar to the cecropins and polymyxins, as shown in Table 3.

Figure 5:
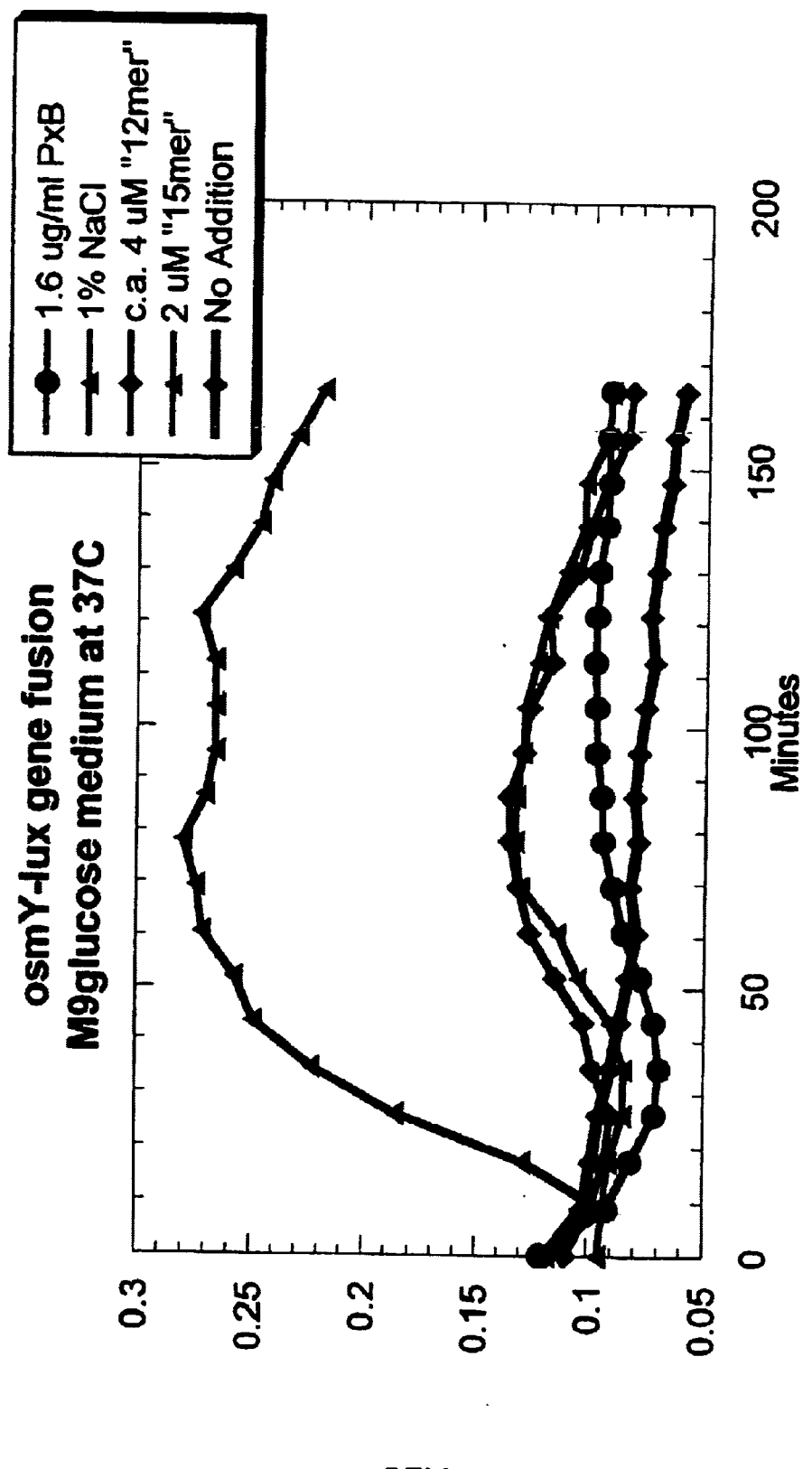
FIGS. 5 and 6 represent graphs that illustrate results of tests of the antibacterial properties of peptides according to the present invention.
Figure 6:
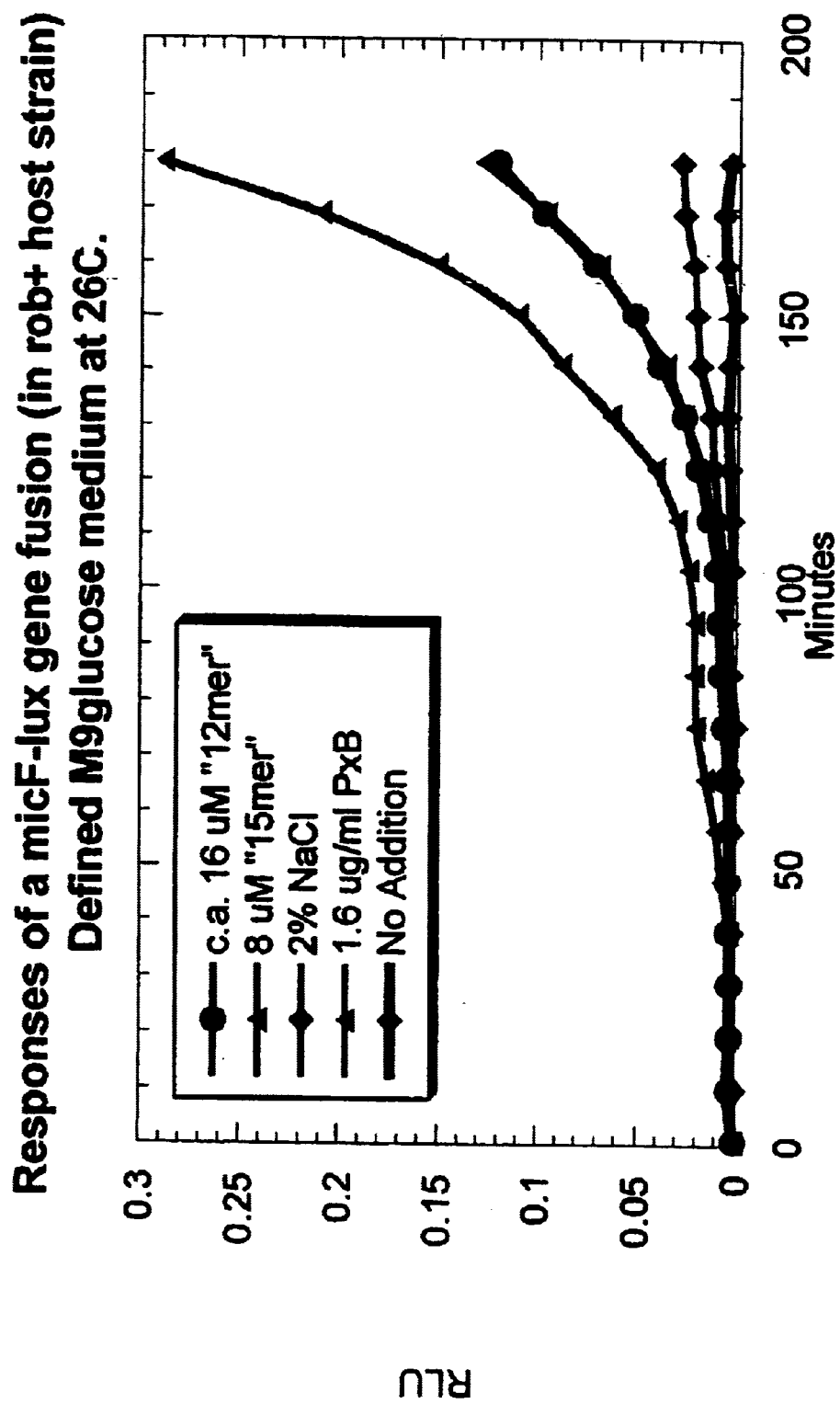

The bioluminenescence data result from test carried out according to U.S. Pat. No. 5,683,868, Highly Sensitive Method For Detecting Environmental Insults, issued Nov. 4, 1997 to LaRossa et al., the entire contents of the disclosure of are hereby incorporated by reference, The tests described in this patent permit antibacterial properties of peptides or any other materials to be assessed. FIGS. 5 and 6 illustrate test results demonstrating the antibacterial properties of the peptides. Along these lines, FIG. 5 illustrates a relationship between relative light units and minutes of exposure of bacteria to the various materials in the legend. PxB represents polymyxin, a known antibacterial material. In the graph, a decrease in RULs corresponds to a decrease in bacteria. As can be seen in FIG. 5, a peptide according to the present invention, where n is 5 produces similar results to the PxB. FIG. 6 illustrates the results of another study, These graphs demonstrate the antibacterial properties of the peptides. Table 4 below summarizes the results of some of these tests.

TABLE 4

| Gene fusion | Stress sensed | Regulatory gene | Osmotic shock (NaCl) | Polymyxin | (hAla-hLys-hVal)$_4$ | (hAla-hLys-hVal)$_5$ |
|---|---|---|---|---|---|---|
| micF | N/A | Rob | yes | yes | yes | yes |
| osmY | osmotic shock | (not ROB) | yes | yes | yes | yes |

Experimental Methods And Materials For Group II Peptides 1 and 2

Fmoc α-amino acid pentafluorophenyl esters were purchased from Nova Biochem, HBTU and HOBt from Advanced ChemTech., Fmoc PAL-PEG-PS resin (loading 0.17 mmol/g) from PerSeptive Biosystems, SOPC and SOPS from Avanti Polar-Lipids, Inc., Calcein from Lancaster Synthesis, Triton X-100 from, and all other reagents from Aldrich and were used without further purification. All Fmoc,-amino acids were synthesized from the corresponding Fmoc α-amino acid pentafluorophenyl esters via Arnst-Eistert homologation following Seebach's published procedure (see International Patent Document WO 97/47593 to Seebach). Peptides were synthesized in a standard glass peptide synthesis vessel. The purification was carried out on a Waters HPLC using a Vydac C4 column. Solvent A was composed of 1% TFA in water a n d solvent B was composed of 90% acetonitrile, 10% water and 0.1% TFA. Mass spectra were measured on a Hewlett-Packard 1100 ESI spectrometer and a PerSpective Biosystems Voyager-DERP MALDI-TOF mass spectrometer. NMR spectra were obtained on a Bruker AC-250 spectrometer. UV-Vis spectra were measured on a Hewlett-Packard 8453 spectrometer. Fluorescence measurement was carried out on a a Hitachi F-2500 Fluoresence spectrophotometer. CD spectra were obtained on an AVIV 62DS spectropolarimeter.

Synthesis Of H-(HAla-HLys-HVal)$_n$—NH$_2$ (n=4, 5)

Fmoc PAL-PEG-PS resin (588 mg, 0.1 mmol) was swell in DMF (5 mL) for 30 min before the synthesis. The Fmoc was deprotected with 20% piperidine/DMF (3×5 mL x 5 min), and washed with DMF (5×5 mL x 2 min). Amino acid coupling was carried out by adding 2 mL solution of amino acid (0.25 mmol), HBTU (95 mg, 0.25 mmol), HOBt (34 mg, 0.25 mmol), DIEA (139 µL, 0.8 mmol) in DMF to the resin, shaking for 4 h, and washing with DMF (5×5 mL×2 min). The peptides were cleaved from the resin by treatment of TFA/TIS (95:5) for 2 h. The solution was concentrated and the peptide was precipitated out with addition of cold ether. Peptides were purified by HPLC on a reverse phase C4 column, with a linear gradient from 20% to 50% solvent B in 50 min for n=4, and from 30% to 60% solvent B in 60 min for n=5. LRMS (MALDI-TOF) m/e calculated for n=4 $C_{68}H_{132}N_{17}O_{12}$ (MH+) 1379.1, found 1379.6. LRMS (MALDI) m/e calculated for n=5 $C_{85}H_{164}N_2O_{15}$ (MH$^+$) 1719.4, found 1720.1.

Circular Dichroism Studies

CD spectra were measured on an AVIV 62DS spectropolarimeter using both 1 mm and 10 mm quartz cuvettes. Sample stock solutions were prepared in water and diluted into appropriate buffers. Peptide concentrations were determined from the dry weight of lyophilized peptide, and were calibrated by the UV absorbance of Fmoc before the deprotection.

Hemolysis Assay

Hemolysis experiments were carried out by incubating 0.25% suspension of human erythrocytes (RBC's) with peptides of different concentrations in 150 mM sodium choloride, 10 mM Tris buffer, pH 7.0. The sample was prepared by combining 400 μL of the RBC suspension and 100 μM of the peptide solution. After incubated the sample at 37_ C. for 1 hour, the sample was centrifuged at 14,000 rpm for 5 min, and the $OD_{414}$ of the supernatant was measured. Mellitin (50 μM) was used to get 100% hemolysis. The hemolytic IC50 was obtained by plotting hemolysis percentage vis. peptide concentration, and the concentration required for 50% hemolysis was determined from the smooth curve-fitted graph.

Antibacterial Assay

Antibacterial assay was performed by incubation of K 91 *E. coli* and peptide of different concentrations in minimal media, at pH 7.4. The peptide solution (50 μL) and K 91 *E. coli* culture (20 μL, grown in minimal media for 24 hr–36 hr) were mixed with 1 mL minimal media. After incubation at 37° C. for 8 hr, the $OD_{600}$ was measured. The peptide dose required for 50% suppress of bacterial growth was obtained from the smooth fitted $OD_{600}$ vs. log[peptide] curve.

Peptide Binding to Phospholipid Bilayers

The binding affinity of peptides to phospholipid bilayers was measured using CD spectra of the peptide in the presence of varying lipid vesicle concentrations. Peptides show little structure from CD spectra in water. Upon addition of lipid vesicles, the ellipiticity at 214 nm increased as a consequence of helix formation due to interactions between the peptide and lipid surface. Small unilamellar vesicles (SUV) of SOPC/SOPS were prepared by sonicating lipid large vesicles in 10 mM phosphate buffer, pH 7. CD spectra were taken before and after the addition of aliquots of vesicle to 2 mL peptide solution in 10 mM phosphate buffer, pH 7.

The dissociation constant Kd was determined from equation (1) for single site binding:

$$[P](R-1)-c/n-Kd+c/(nR)=0 \quad (1)$$

where [P] and c are peptide and lipid molar concentrations, respectively, n is the number of lipids per peptide binding site. R is the fraction of peptide bound, which can be calculated from equation (2):

$$R=(\theta_c-\theta_0)/(\theta_s-\theta_0) \quad (2)$$

where $\theta_c$ and $\theta_0$ are the ellipticities at 214 nm at lipid concentration of c and o, respectively, $\theta_{max}$ represents the ellipticity at 214 nm of saturated binding. Since lipid vesicles cause light scattering, it was difficult to obtain accurate values for $\theta_s$. Therefore $\theta_s$ was considered as a variable during the curve fitting. Curve fitting was done by using KaleidaGraph program.

Peptide-Induced Leakage of Liposomal Contents

The leakage of liposome contents to the external media was monitored by the release of calcein encapsulated in vesicles. The vesicle was prepared by reverse-phase evaporation in 10 mM sodium phosphate buffer, pH 7, followed by single extrusion through one 0.2 μm pore size polycarbonate filter. The non trapped calcein was removed by eluting through a size exclusion Sephadex G-25 column, with 90 mM sodium chloride, 10 mM sodium phosphate, pH 7. The leaking kinetics was monitored by follow the increase of calcein fluorescence intensity at 520 nm (excitation at 490 nm) due to release of self-quenching. The experiment was carried out on a Hitachi F-2500 Fluoresence spectrophotometer, with a slit width of 5 μm. The initial rate was calculated from the linear part of the %leakage vs. time curve.

Antibacterial Assay and Hemolysis Experiment

The activity and selectivity of peptide 1 and peptide 2 were examined by antibacterial assay and hemolysis experiments. E. Coli and human erythrotytes (RBC) were used as models for bacterial cell and mammalian cell, respectively. The peptide concentration required for 50% bacterial growth suppression (IC50), and peptide concentration required for 50% RBC lysis (HD50) are listed in Table 3. Both peptides show high antibacterial activity with IC50 of several μMs, which is comparable to the natural antibacterial peptide magainin (MIC3.2 μg/ml), and the "β-17" beta peptide (MIC6.3 μg/ml) recently reported from Gellman and coworkers (see Porter et al., NATURE, 2000, 404, 565). The antibacterial activities of peptide 1 and peptide 2 are about the same except peptide 2 has slightly lower IC50. Similar trend has been observed in the previous study, that longer peptide tends to have higher activity. However, the difference in IC50 is much smaller for this series of peptide than the previously studied ones. Antibacterial peptide with good selectivity is usually represented by its low hemolysis ability. Our results from hemolysis experiment indicate that selectivity of this series of peptide is greatly improved compared to the previous studied ones. The HD50 is 670 μM for peptide 1 and 240 μM for peptide 2, which gives a selectivity of 111 for peptide 1 and 60 for peptide 2.

TABLE 5

|  | Peptide 1 (n = 4) | Peptide 2 (n = 5) |
| --- | --- | --- |
| IC50 | 6 | 4 |
| HC50 | 670 | 240 |
| selectivity | 111 | 60 |
| Kd (SOPS/SOPC (1:9)) | 1.4 | 0.3 |
| Kd (SOPC) | — | 15 |

Membrane Binding Studies

Figure 2:
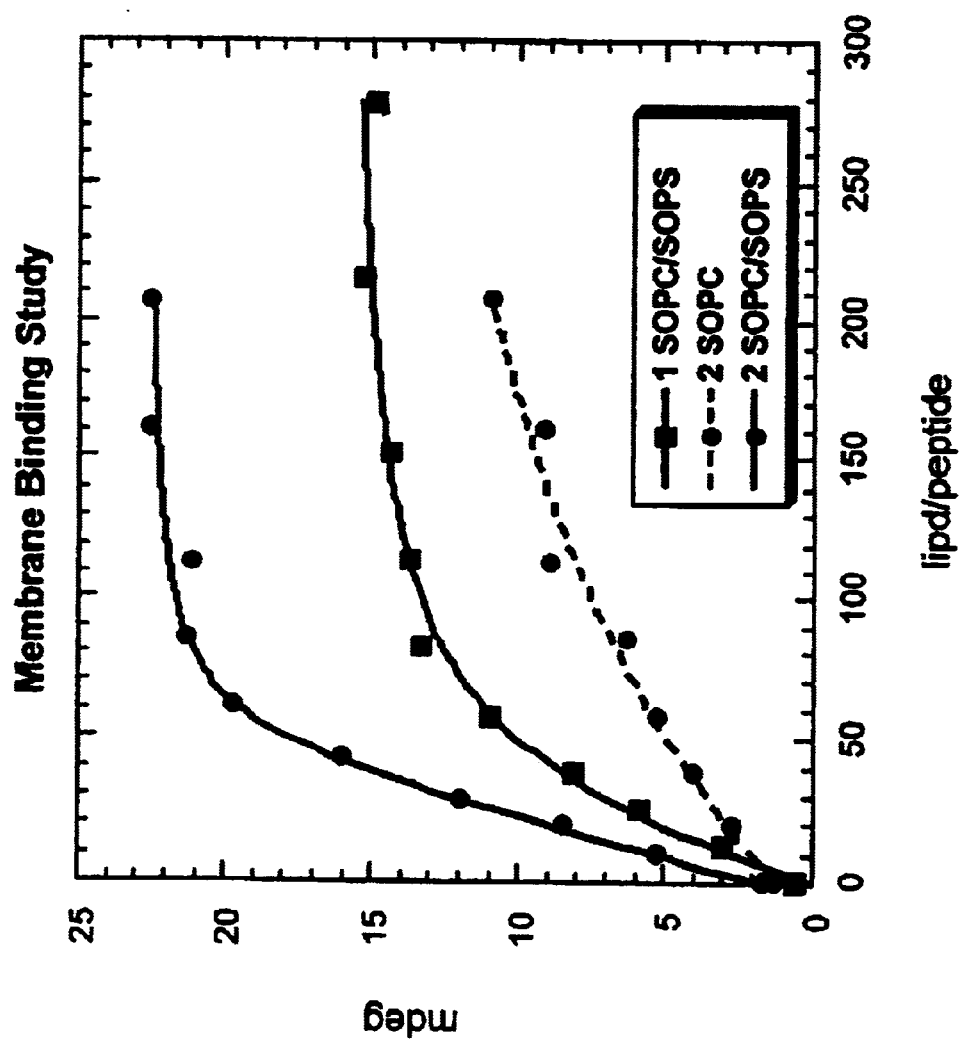
FIG. 2 represents a graph that illustrates results of membrane binding studies carried out on compounds 1 and 2 of group II of compounds according to the present invention.

To get better understanding of the binding mechanism of the peptides to lipid membranes, the dissociation constants (Kd) of peptide 1 and peptide 2 to small unilamellar lipid vesicles (SUV) were measured. Since binding to DPC micelle drives peptide 1 and peptide 2 from random coil conformation to helical conformation, the binding equilibrium can be monitored by CD spectroscopy. The binding curve obtained from CD measurement is shown in FIG. 2, and the dissociation constant Kd derived from curve fitting with single site binding equation is listed in Table 1. Small unilamellar vesicles (SUV) were used as lipid bilayer model. Mammalian cell membranes mainly consist of charge neutral phosphocholin, while bacterial outer membranes have more negative charges coming form lipopolysaccharide or presence of teichoic and teichuronic acids, and of amino acid carboxyl groups in the multilayered peptidoglycan. In order to mimic bacterial, 10% negative charged phosphoserine (SOPS) was mix with SOPC to generate SUVs. Both peptides exhibit tight binding to SOPS/SOPC (1:9) vesicles. With an equivalence of 42 lipid molecules per peptide molecule, a Kd of 1.4 μM was obtained for peptide 1. For each peptide 1, the surface area for binding is 188 Å$^2$, the corresponding area access for binding from the outer leaflet of the lipid bilayer is 65 Å$^2$×21=1365Å$^2$. Thus the ratio of areas is 7.3:1 (lipid:peptide). Presumably, the ratio is the same for both peptide 1 and peptide 2. Using an equivalence number of 52 for peptide 2, a Kd of 0.3 μM was obtained for SOPS/SOPC (1:9). The longer peptide binds tighter than the shorter one. But the difference is small, just like the IC50 values of peptide 1 and peptide 2. Vesicles of phosphocholin (POPC and SOPC) were used as models of mammalian cell membrane, peptide 1 does not show any formation of helix while peptide 2 shows increase of helix content. The Kd of peptide 2 to SOPC LUV is 15 μM. The much lower affinity of peptide 2 to SOPC vesicles than to SOPS/SOPC (1:9) vesicles explains its selective activity against bacterial cells. The failure to bind SOPC vesicles of peptide 1 elucidates its better selectivity than peptide 2.

Peptide-Induced Leakage of Liposomal Contents

Figure 3:
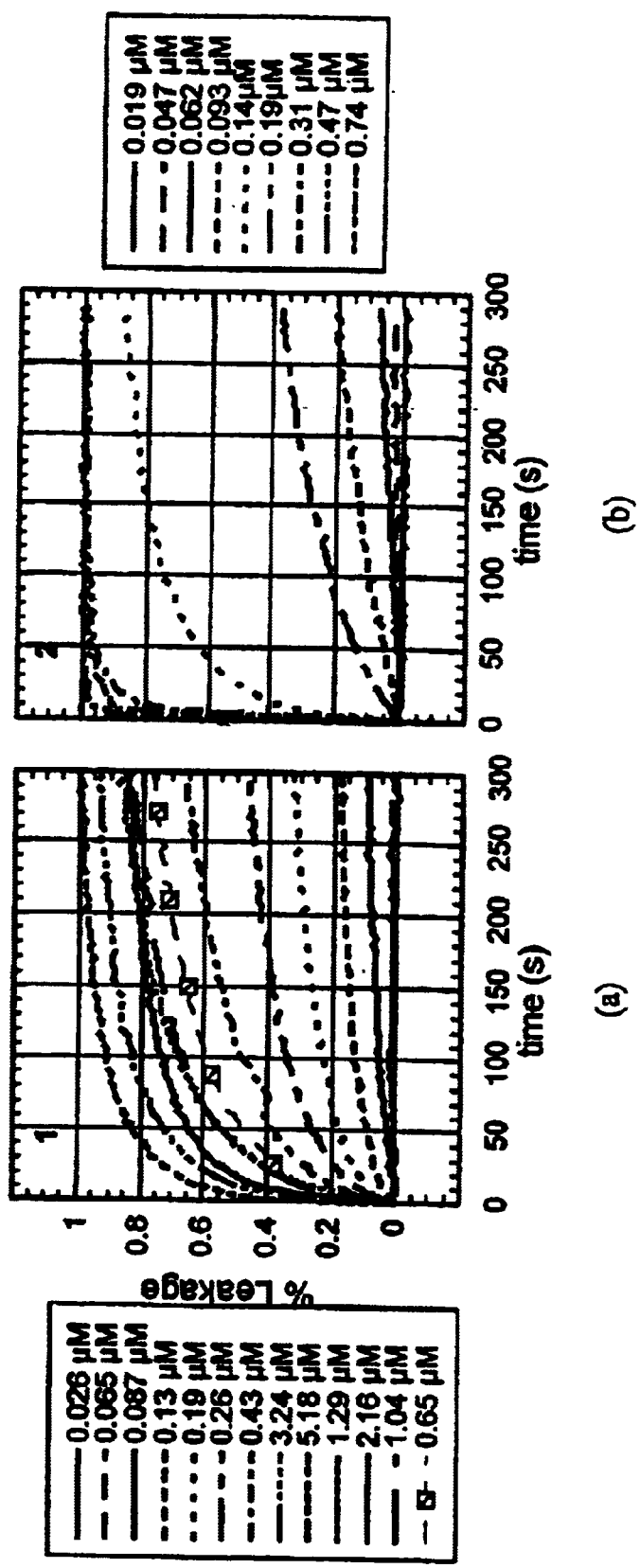
FIGS. 3a and 3b represent graphs that illustrate relationships between percent leakage and time demonstrating results of tests of peptide induced leakage of liposome contents carried out with compounds 1 and 2 of group II of compounds according to the present invention.
Figure 4:
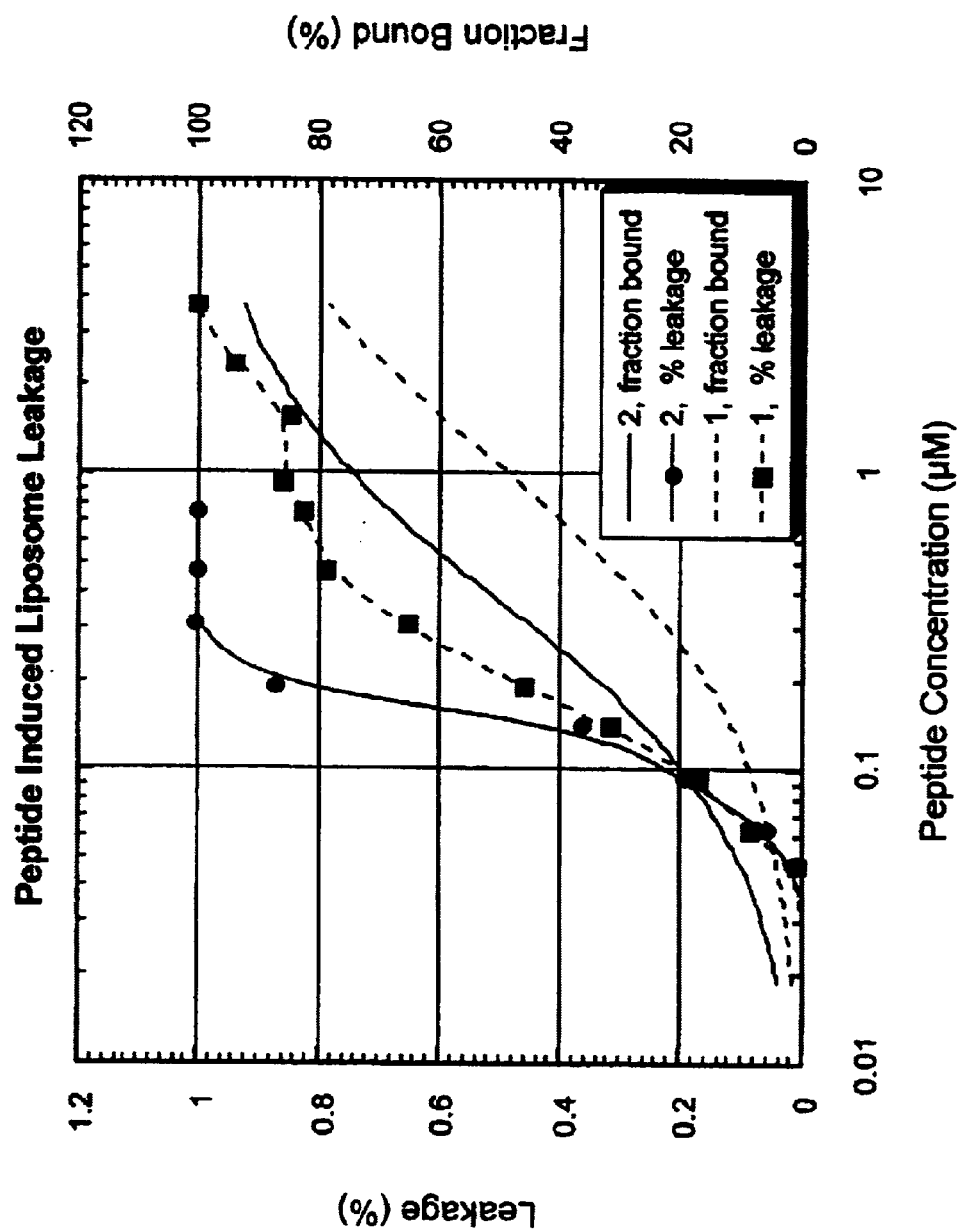
FIG. 4 represents a graph that illustrates relationships between percent leakage and peptide concentration and fraction bound and peptide concentration demonstrating results of tests of peptide induced leakage of liposome contents carried out with compounds 1 and 2 of group II of compounds according to the present invention.

The mechanism of how the antibacterial peptides work is still on debate. However, it is generally believed they kill the cell by disturbing cell membranes. The experiment of peptide-induced leakage of liposomal contents is a direct way to monitor this process. Large unilammilar vesicles (LUV) of SOPS/SOPC (1:9) were used in the binding study. The leakage of encapsulated calcein was detected by its fluorescence at 515 nm. The leakage percentage vs. time is shown in FIG. 3. The percentage of leakage at 285 seconds was plotted vs. peptide concentration and was shown in FIG. 4. The fraction of bound lipid at different peptide concentration was calculated and overlaid in FIG. 4 as well. The lysis abilities of the two peptides are similar at low peptide concentration, and become quite different with increasing amount of peptide. As shown in FIG. 4, both peptides can not induce leakage of the vesicle when the peptide concentration is below 0.05 μM. With increase of peptide concentration, the leakage percentage increases quickly. For peptide 2, the leakage percentage jumps to 100% within the range between 0.05 μM and 0.14 μM where the corresponding fractions of lipid bound are about 10% 40%, respectively. A relatively slower change was observed for peptide 1. The percentage of leakage increases to about 80% when the peptide concentration reaches 0.5 μM. The lysis ability stays at a plateau until the peptide concentration is pushed up to 2 μM, when about 60% of lipid molecules are bound to peptide molecules. Complete lysis of the vesicle at 285 seconds is induced when 5 μM of peptide 1 was added, and the calculated lipid bound fraction is about 80%. The difference between the two peptides is even more obvious when looking at the leakage rate right after the addition of peptide to the vesicle solution, as shown in FIG. 3. The initial leakage rate for peptide 2 increases sharply when the peptide concentration increases from 0.14 μM to 0.19 μM. Complete lysis of the vesicle is finished within 20 s with peptide concentration higher than 0.5 μM. For peptide 1, the leakage initial rate increases in a continuous fashion, and 100% leakage is not complete until 300 s with 5.18 μM peptide.

Numerous studies on natural antibacterial peptides have revealed that the distribution of hydrophobic face and polar face on their amphiphilic structure account for their selectivity. Increased hydropobicity of a peptide can increase its binding affinity to the charge neutral membrane of mammalian cells, thus reducing the selectivity of this peptide. Group II peptides 1 and 2 are less hydrophobic than the peptides of Group I. This may at least in part result from replacement of residues homo-Leucine and homo-Valine in the peptides of Group I with less hydrophobic homo-Alanine. The results from the antibacteria assay and hemolysis experiment indicate that by reducing the hydrophobicity of the peptide, the selectivity is remarkably enhanced.

The functional mechanism is thought to be different for peptide 1 as compared to peptide 2. For example, the binding study shows that peptide 2 has a higher affinity to SOPS/SOPC vesicles than peptide 1. In addition, peptide 2 can bind weakly to charge neutral SOPC, while peptide 1 cannot. This suggests that due to its longer size, peptide 2 has higher overall hydrophobicity, or its helical structure is more stable. The higher affinity to lipid bilayer of peptide 2 reduces its ability to differentiate bacterial cell from mammalian cell, thus lowering its selectivity.

Two mechanisms have been proposed for the cell killing process by antibacterial B-peptide. In the carpet mechanism, peptides aggregate parallel on the membrane surface, The accumulated peptide molecules wrap the membrane surface in a carpet-like manner, and causes the membrane thinner and eventually produce cavities after the peptide concentration reaches to a threshold value. The so-called barrel-stave mechanism suggests that the bound peptides on the cell surface self associate into helix bundles, and insert into the membrane to form cores on it. The latter mechanism is more suitable for hemolytic toxins such as mellitin, whose sequence is more helix stabilizing. It becomes more likely that the two mechanisms are two aspects of the real process. From experiments investigating peptide-induced leakage of liposomal content, the two peptides behave through similar mechanism. When peptide concentration is over 0.05 μM, they cause leakage of the vesicle, and the lysis ability increases gradually with increased amounts of peptide. However, when peptide concentration is more than 0.1 μM, the lysis ability of peptide 2 increases sharply in a cooperating manner, when less than half of the lipid molecules are peptide bound. This suggests a second binding site for peptide 2. The second site may come from the self-association of peptide 2 after deposit on the membrane. In contrast, the lysis ability of peptide 1 increases in a more gradual way corresponding to concentration increase. The carpet mechanism is more suitable to be used to describe this process. There may be formation of small aggregates of peptide 1 when the peptide concentration is high and the first binding site is close to saturation. Peptide 2 functions similarly as peptide 1 at very low peptide concentration. After the bound fraction of lipid reaches more than about 40%, the peptides very likely oligomerize on the membrane and induce leakage in the barrel-stave fashion. The threshold may actually be less than 40%. The CD of peptide 2 in aqueous solvent with high phosphate concentration indicates helix formation, suggesting its tendency to self-associate when the electrostatic repulsion gets diluted.

It appears as if a length of 14 residues is favorable for selectivity of this peptides according to the present invention. Magainin differentiates bacterial cells from mammalian cells at a level of 300 times. Values for the peptides according to the present invention are close to this value. Additionally, the peptides according to the present invention may be altered to step closer to or exceed natural antibacterial peptides. The changes may be so as to generate peptides with more diversity in the sequence so as to achieve the best balance.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. An antibacterial β-peptide having the following formula:

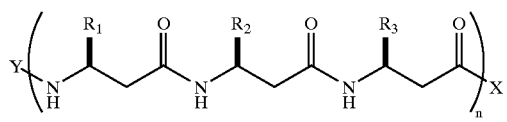

wherein

R$_1$ is H, an alkyl group having 1–4 carbon atoms, phenyl, heteroaryl, or an alkyl-aryl;

R$_2$ is an amine-containing alkyl group having the formula —(CH$_2$)$_m$NH$_2$, wherein m=1, 2, 3, 4, or 5, (CH$_2$)$_x$NHC=NHNH$_2$ wherein x is 1, 2, 3, 4, or 5, a pyridyl, an alkylpryidyl, an amidine-substituted benzyl, a phenyl group, or a cyclic amidine;

R$_3$ is H, an alkyl group having 1–4 carbon atoms, phenyl, heteroaryl, or an alkyl-aryl;

X is —NH$_2$, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and n is 2, 3, 4, 5, 6, or 7;

wherein at least one of X and Y is a polymer selected from the group consisting of polyurethane, polyetherurethane, polyester, silicone, polyamide, polyolefin, polystyrene, polypeptide, polysaccharide, cellulosic, and silk.

2. The β-peptide according to claim 1, wherein at least one of X and Y further includes at least one α-amino acid attached to the peptide.

3. The β-peptide according to claim 1, wherein the β-peptide is linked to the polymer by a non-cleavable linker.

4. The β-peptide according to claim 1, wherein the peptide can form a L+2 helix.

5. The β-peptide according to claim 1, wherein the alkyl groups of R$_1$ and R$_3$ are methyl, ethyl, n-propyl, i-propyl, n-butyl, sec-butyl, or tert-butyl.

6. The β-peptide according to claim 1, wherein the β-peptide is non-covalently bonded to a carrier.

7. The β-peptide according to claim 6, wherein the carrier is a sol-gel or an aero gel.

8. An antibacterial β-peptide having the following formula:

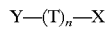

wherein n is 2, 3, 4, 5, 6, or 7;

X is —NH$_2$, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and T is a triplet comprising T1-T2-T3, wherein T1 comprises a hydrophobic β-amino acid, T2 comprises a polar or basic amino acid, T3 comprises either a hydrophobic β-amino acid or a polar or basic β-amino acid, wherein at least one-half of the number of triplets includes a basic β-amino acid;

wherein at least one of X and Y is a polymer selected from the group consisting of polyurethane, polyetherurethane, polyester, silicone, polyamide, polyolefin, polystyrene, polypeptide, polysaccharide, cellulosic, and silk.

9. The β-peptide according to claim 8, wherein at least one of X and Y further includes at least one α-amino acid or at least one β-amino acid attached to T.

10. The β-peptide according to claim 9, wherein the at least one β-amino acid is selected from the group consisting of a hydrophobic, polar, and basic β-amino acid.

11. The β-peptide according to claim 8, wherein the β-amino acids are substituted at at least one of C2 and C3 with a substituent comprising aryl, or a C1-10 straight or branched, linear or cyclic, substituted or unsubstituted alkane, alkene, or alkyne, —H, —CH$_3$, —CH(CH$_3$)$_2$, —CH$_2$—CH(CH$_3$)$_2$, —CH(CH$_3$)CH$_2$CH$_3$, —CH$_2$-phenyl, —CH$_2$-pOH-phenyl, —CH$_2$-indole, —CH$_2$—SH, —CH$_2$—CH$_2$—S—CH$_3$, CH$_2$OH, —CHOH—CH$_3$, —CH$_2$—CH$_2$—CH$_2$—NH$_2$, —CH$_2$—CH$_2$—CH$_2$—NH—C(NH)NH$_2$, —CH$_2$-imidazole, —CH$_2$—COOH, —CH$_2$—CH$_2$—COOH, —CH$_2$—CONH$_2$, —CH$_2$—CH$_2$—CONH$_2$, or together with an adjacent —NH group forms a proline amino acid residue, and wherein the stereochemistry of the β-peptide is in an aldol configuration.

12. The β-peptide according to claim 11, wherein at least one of the substituents is substituted and the substituent on the substituent is aryl, or a C1-10 straight or branched, linear or cyclic alkane, alkene, or alkyne, —H, —CH$_3$, —CH(CH$_3$)$_2$, —CH$_2$—CH(CH$_3$)$_2$, —CH(CH$_3$)CH$_2$CH$_3$, —CH$_2$-phenyl, —CH$_2$-pOH-phenyl, —CH$_2$-indole, —CH$_2$—SH, —CH$_2$—CH$_2$—S—CH$_3$, CH$_2$OH, —CHOH—CH$_3$, —CH$_2$—CH$_2$—CH$_2$—CH$_2$—NH$_2$, —CH$_2$—CH$_2$—CH$_2$—NH—C(NH)NH$_2$, —CH$_2$-imidazole, —CH$_2$—COOH, —CH$_2$—CH$_2$—COOH, —CH$_2$—CONH$_2$, —CH$_2$—CH$_2$—CONH$_2$, or together with an adjacent —NH group forms a proline amino acid residue.

13. The β-peptide according to claim 8, wherein the β-peptide is non-covalently bonded to a carrier.

14. The β-peptide according to claim 13, wherein the carrier is a sol-gel or an aero gel.

15. The β-peptide according to claim 8, wherein each T is the same.

16. The β-peptide according to claim 8, wherein the peptide comprises a copeptide including repeating groups of triplets wherein each triplet is not the same.

17. An antibacterial composition, comprising:

an antibacterial β-peptide having the following formula

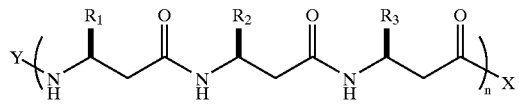

wherein

R$_1$ is H, an alkyl group having 1–4 carbon atoms, phenyl, heteroaryl, or an alkyl-aryl;

R₂ is an amine-containing alkyl group having the formula —(CH₂)$_m$NH₂, wherein m=1, 2, 3, 4, or 5, (CH₂)$_x$NHC=NHNH₂ wherein x is 1, 2, 3, 4, or 5, a pyridyl, an alkylpryidyl, an amidine-substituted benzyl, a phenyl group, or a cyclic amidine;

R₃ is H, an alkyl group having 1–4 carbon atoms, phenyl, heteroaryl, or an alkyl-aryl;

X is —NH₂, —OH, —NHR, or OR where R is alkyl aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and n is 2, 3, 4, 5, 6, or 7; and a carrier, wherein the β-peptide is covalently bonded to the carrier.

18. An antibacterial β-peptide having the following formula:

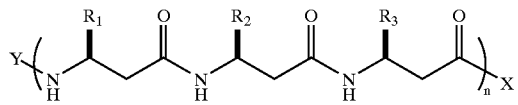

wherein R₁ is H, an alkyl group having 1–4 carbon atoms, phenyl, heteroaryl, or an alkyl-aryl;

R₂ is an amine-containing alkyl group having the formula —(CH₂)$_m$NH₂, wherein m=1, 2, 3, 4, or 5, (CH₂)$_x$NHC=NHNH₂ wherein x is 1, 2, 3, 4, or 5, a pyridyl, an alkylpryidyl, an amidine-substituted benzyl, a phenyl group, or a cyclic amidine;

R₃ is H, an alkyl group having 1–4 carbon atoms, phenyl, heteroaryl, or an alkyl-aryl;

X is —NH₂, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and n is 2, 3, 4, 5, 6, or 7;

wherein the β-peptide is non-covalently bonded to a carrier, wherein the carrier is a sol-gel or an aero gel.

19. An antibacterial β-peptide having the following formula:

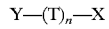

wherein n is 2, 3, 4, 5, 6, or 7;

X is —NH₂, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and T is a triplet comprising T1-T2-T3, wherein T1 comprises a hydrophobic β-amino acid, T2 comprises a polar or basic amino acid, T3 comprises either a hydrophobic β-amino acid or a polar or basic β-amino acid, wherein at least one-half of the number of triplets includes a basic β-amino acid;

wherein the β-peptide is non-covalently bonded to a carrier, and wherein the carrier is a sol-gel or an aero gel.

20. An antibacterial peptide having the following formula:

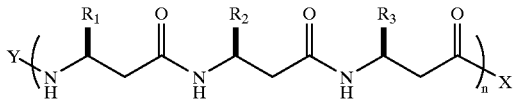

wherein

R₁ is H, an alkyl group having 1–4 carbon atoms, phenyl, heteroaryl, or an alkyl-aryl;

R₂ is an amine-containing alkyl group having the formula —(CH₂)$_m$NH₂, wherein m=1, 2, 3, 4, or 5, (CH₂)$_x$NHC=NHNH₂ wherein x is 1, 2, 3, 4, or 5, a pyridyl, an alkylpryidyl, an amidine-substituted benzyl, a phenyl group, or a cyclic amidine;

R₃ is H, an alkyl group having 1–4 carbon atoms, phenyl, heteroaryl, or an alkyl-aryl;

X is —NH₂, —OH, —NHR, or OR where R is alkyl, aryl or acyl groups either free or polymer-supported, a carboxamide, a substituted carboxamide, or a polymer;

Y is H, an alkyl group, an acyl group, an acyl-terminated polymer, a sulphonamide, an ether, a urea, a urethane, or a polymer; and n is 2, 3, 4, 5, 6, or 7;

and further comprising at least one α-amino acid arranged between at least one of X and the peptide and at least one of Y and the peptide.

* * * * *